United States Patent [19]

Murakami et al.

[11] Patent Number: 4,608,598

[45] Date of Patent: Aug. 26, 1986

[54] THERMAL IMAGING APPARATUS

[75] Inventors: Yoshishige Murakami, Yokohama; Takeshi Inoue; Atsushi Tanaka, both of Sagamihara, all of Japan

[73] Assignee: Fujitsu Limited, Kawasaki, Japan

[21] Appl. No.: 625,683

[22] Filed: Jun. 28, 1984

[30] Foreign Application Priority Data

Jun. 29, 1983 [JP] Japan ................................ 58-117253

[51] Int. Cl.⁴ ............................................... H04N 7/18
[52] U.S. Cl. ..................... 358/113; 358/134; 358/140; 358/183
[58] Field of Search ................ 358/93, 113, 140, 183, 358/134; 128/660, 661

[56] References Cited

U.S. PATENT DOCUMENTS

| | | | |
|---|---|---|---|
| 3,954,098 | 5/1976 | Dick | 128/661 |
| 4,199,785 | 4/1980 | McCullough | 358/113 |
| 4,218,707 | 8/1980 | Reed | 358/113 |
| 4,399,464 | 8/1983 | Hix | 358/113 |
| 4,423,737 | 1/1984 | Yano | 128/661 |

FOREIGN PATENT DOCUMENTS

| | | |
|---|---|---|
| 0023131 | 1/1981 | European Pat. Off. |
| 0026673 | 4/1981 | European Pat. Off. |
| 2940536 | 5/1981 | Fed. Rep. of Germany |
| 1278671 | 6/1972 | United Kingdom |

Primary Examiner—Howard W. Britton
Attorney, Agent, or Firm—Staas & Halsey

[57] ABSTRACT

A plurality of thermal images of an observed object at different times are simultaneously displayed on a single screen of a television monitor simply and economically. The thermal imaging apparatus includes an infrared camera to scan the observed object and to produce a detected video output, a TV monitor to display the thermal images, and a hard memory to convert the IR camera scan to the TV monitor display. The capacity of the hard memory is kept at a minimum which is sufficient for memorizing image data of one frame of scanning. For simultaneously display of plural images, the IR camera scans so that the observed object is in a limited part of the field of view, to produce a detected video output with limited video signals corresponding to the limited part of the field of view, and the hard memory writes the limited signals in a limited part of the hard memory corresponding to the limited part of the field of view, as limited image data, at the scan speed of the IR camera, so that the limited image data taken at each respective time is memorized in the hard memory. All the image data memorized in the hard memory are then read out at the TV displaying speed and simultaneously displayed on the TV monitor screen.

10 Claims, 7 Drawing Figures

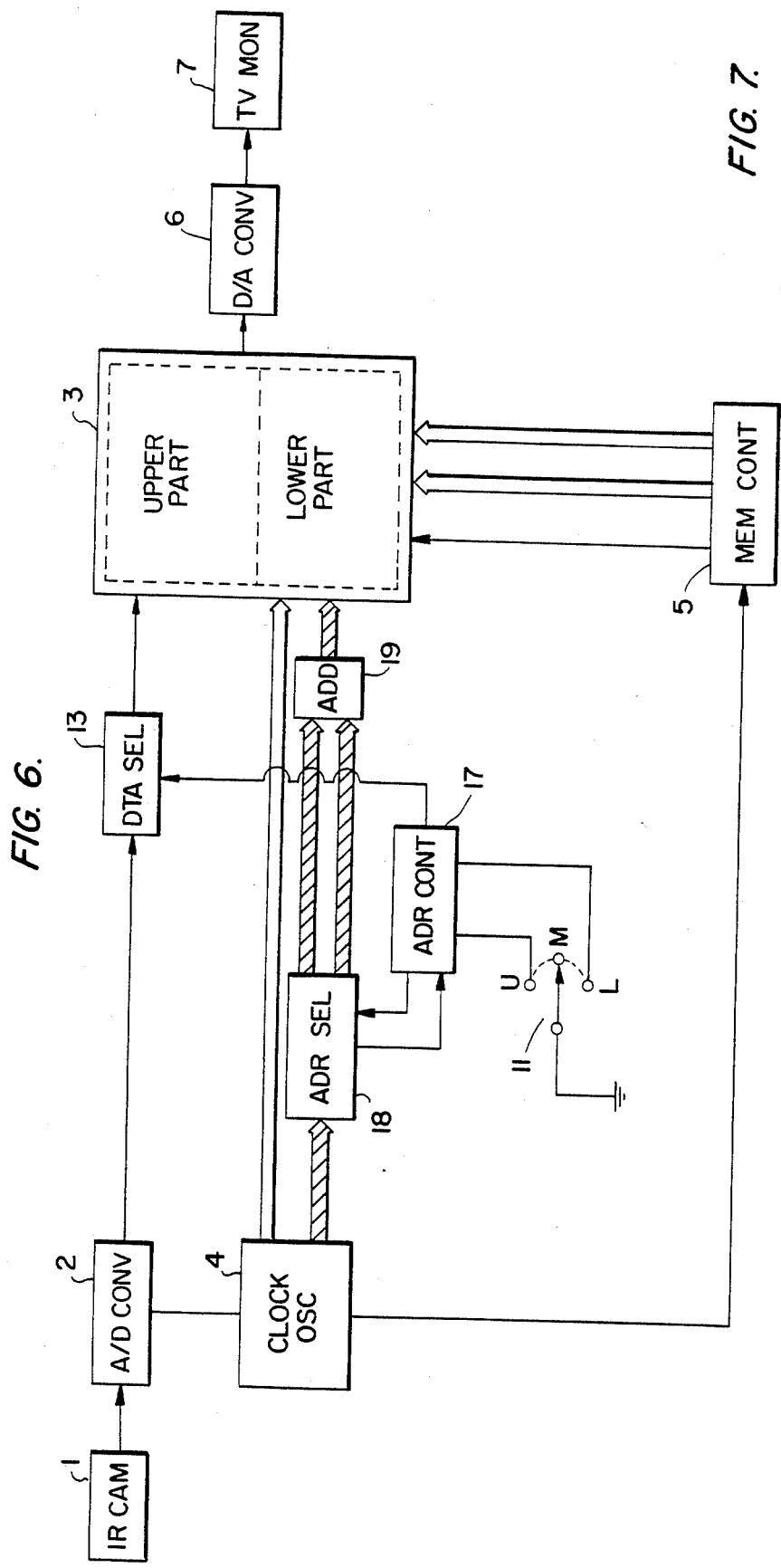
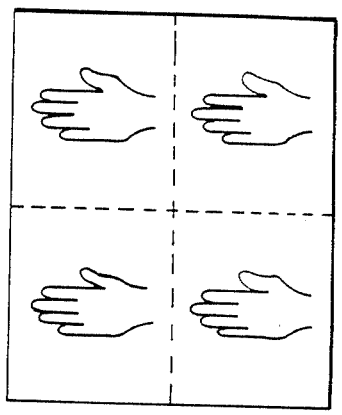
FIG. 6.
FIG. 7.

THERMAL IMAGING APPARATUS

BACKGROUND OF THE INVENTION

The present invention relates to a thermal imaging apparatus, by which a plurality of thermal images of an observed object corresponding to different times are simultaneously displayed on respective parts of a television monitor screen, to allow obtaining more information concerning the object from the combination of the thermal images, by comparing them with each other.

A thermal imaging apparatus provides a thermal image by receiving passively the infrared radiation from an observed object with an infrared sensor or detector. The technology concerning the thermal imaging apparatus has become known as "thermography", and is useful in the medical and industrial fields for non-invasive diagnosis and non-destructive examination.

The thermal imaging apparatus generally provides a thermal image by means of an optical scan and an electronic display which are synchronized with each other. However, the optical scanning speed cannot be increased as high as the television (TV) scanning speed because of the well known thermography principle. Therefore, a conversion technique which converts the speed of the optical scan to that of the TV display is required to observe and record thermal images using a conventional TV monitor and a video tape recorder.

The conversion can be provided using a memory device, such as a hard memory formed of a semiconductor integrated circuit (IC memory). In this case, the signal data detected by the optical scan at relatively slow speed are memorized in the IC memory, and the memorized data are read out and displayed by the TV technique.

In thermography it is often required to check the time variation of the thermal image of an observed object, because the variation provides valuable information. The thermal images at different times will be referred to as the "thermal time images" hereinafter.

In the method of display in the prior art, the variations of the thermal time images could be compared by observing different thermal time images sequentially displayed on the TV monitor. Therefore, when comparison between the thermal time images was required, hard copies of the thermal time images had to be provided, such as photographs.

In a typical imaging apparatus, a method has been employed for simultaneously displaying different images on an electronic displaying device, such as a TV monitor, using a large memory device such as a large IC memory which has a large memory capacity. The method is as follows: the data of each different image is memorized in a respective part of the large IC memory, sequentially, and all the memorized data are read out by the TV technique and simultaneously displayed on respective parts of a TV monitor. With this method, however, a lot of memory elements (dot memories) and a complicated write-in and read-out control means are required. Therefore, is is difficult to economically apply this method to an actual thermal imaging apparatus. Consequently, this has been a major problem for economically realizing simultaneous display of thermal time images on a TV monitor in a thermal imaging apparatus.

SUMMARY OF THE INVENTION

An object of the thermal imaging apparatus of the present invention, therefore, is to simultaneously display in an economical manner the thermal time images of an observed object on a TV monitor.

Another object of the thermal imaging apparatus of the present invention is to reduce the capacity of dot memories such as in the hard memory so as to be just enough to memorize the image data of a single frame of the optical scanning.

Still another object of the present invention is to simplify the control means of the hard memory to write in and read out the image data.

The above objects are accomplished by the thermal imaging apparatus of the present invention which has the following two operational modes:

in an ordinary mode, which may be called a single-mode, the apparatus displays a thermal image of an observed object at the current time on a TV monitor screen using its full size, while the optical scanning direction is controlled so that the observed object is effectively in the middle of the optical scanning field-of-view (FOV); and in a new mode, which is referred to hereinafter as a multi-mode, the apparatus simultaneously displays different thermal time images of an observed object on a TV monitor screen, while the optical scanning direction is controlled so that the observed object is in a limited part of the FOV, such as left or upper half, for example.

By the thermal imaging apparatus of the present invention, the comparison between the thermal time images of an observed object can be simple and economical, and can provide valuable information concerning the object.

BRIEF DESCRIPTION OF THE DRAWINGS

FIG. 6 is a block diagram of another embodiment of the present invention which can simultaneously display two time images on upper and lower parts of the TV monitor screen.

FIG. 7 is an illustration of a thermal image display by still another embodiment of the present invention, which simultaneously displays four thermal images on a TV monitor screen.

DESCRIPTION OF THE PREFERRED EMBODIMENTS

Before disclosing the present invention, a principle of the thermal imaging apparatus, concerning the functions of an optical scan, a hard memory, and a TV display, will be explained for the sake of understanding the present invention.

Figure 1:
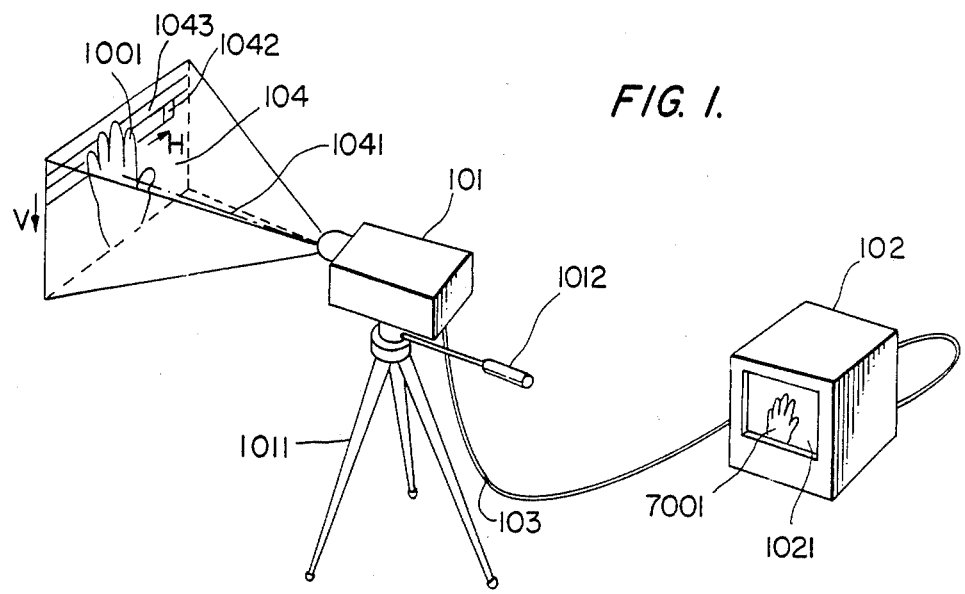
FIG. 1 depicts a typical thermal imaging apparatus.

FIG. 1 depicts a typical thermal imaging apparatus. As shown in the figure, the thermal imaging includes a camera unit 101, a display unit 102, and a connecting cable 103. The camera unit 101 scans a field of view (FOV) 104 with an instantaneous field of view (IFOV) 1042 which receives passively the infrared radiation from the observed object 1001 by an infrared detector which provides the detected video analog signals. The optical scan generally is performed by moving the IFOV 1042 in horizontal and vertical directions sequentially, as shown in FIG. 1. In the figure, reference numeral 1043 is called a horizontal scanning line, and the arrows H and V show the horizontal and vertical movement of the IFOV 1042 respectively. The detected video signals go to the display unit 102 through the connecting cable 103, and a thermal image 7001 of the observed object 1001 is displayed on a TV monitor screen 1021 of the display unit 102. The camera unit 101 is usually mounted on a support such as a tripod 1011, and the direction of the FOV 104 (the direction of a center line 1041 of the FOV 104) can be controlled with the handle 1012 of the tripod 1011, so that the observed object 1001 is placed near the middle of the FOV 104.

As described above, the speed of the optical scan is not so fast as that of a conventional TV display, because, as the speed of the optical scan is increased, the sensitivity of the apparatus decreases. Accordingly, a hard memory is required to convert the speed of the optical scan to that of the TV display, as mentioned above. The hard memory is explained next in reference to FIG. 2.

Figure 2:
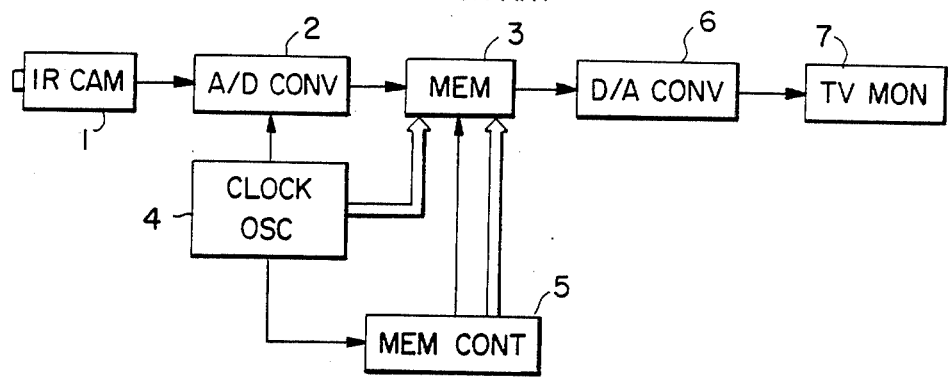
FIG. 2 is a block diagram of a prior art thermal imaging apparatus having a hard memory.

FIG. 2 is a block diagram of a thermal imaging apparatus of the prior art having a hard memory. In the figure, each block is included in the display unit 102 in FIG. 1, except the infrared camera unit IR CAM 1 which corresponds to the camera unit 101 in FIG. 1. Reference numeral 2 is an analog-to-digital converter A/D CONV, 3 is a hard memory MEM, 4 is an input clock oscillator CLOCK OSC, 5 is a memory controller MEM CONT, 6 is a digital to analog converter D/A CONV, and 7 is a television monitor TV MON.

In FIG. 2, the analog video signals from the IR CAM 1 are sequentially supplied to the A/D CONV 2 sequentially following the optical scanning, and are converted to the digital video signals in correspondence with a timing signal from the CLOCK OSC 4. The MEM 3 provides the IC dot memories of a capacity corresponding to the picture elements provided by the IFOV 1042 and the FOV 104 in FIG. 1, and the IC dot memories are arranged horizontally and vertically corresponding to the optical scan. The digital video signals from the A/D CONV 2 are memorized in the MEM 3 as the image data. This memorization can be made under the control of the CLOCK OSC 4 and the MEM CONT 5. That is, the MEM CONT 5 controls the MEM 3 through the illustrated solid-line connection (conventionally indicating series bit data transfer) to switch between the write-in and read-out operations in correspondence with a timing signal from the CLOCK OSC 4, and the CLOCK OSC 4 provides the write-in address signals to the MEM 3 to memorize the digital video signals from the A/D CONV 2 in respective designated addresses corresponding to the picture construction of the FOV 104 shown in FIG. 1.

The MEM CONT 5 also controls the MEM 3 to read out the image data, via the illustrated double-line connection for sending the address control signals. The read-out can be made by the TV scanning technique, and the digital video signals read out from the MEM 3 are converted to the analog video signals by the D/A CONV 6 and are displayed on the TV MON 7 as a TV picture.

Figure 3:
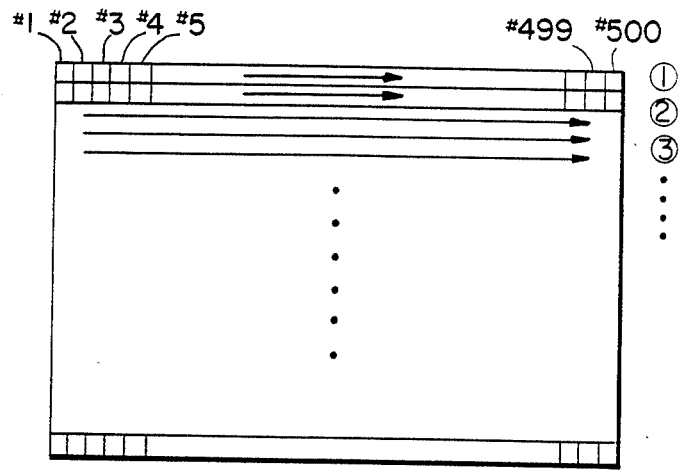
FIG. 3 shows the address arrangement of memory dots in a hard memory whose capacity is just sufficient for memorizing the image data of a single frame of optical scanning in the field-of-view.

FIG. 3 shows an address arrangement of the memory dots in the MEM 3. In the figure, ①,②,③,... show the row (vertical address) of the dot memories corresponding to the scanning line 1043 in FIG. 1, and each row, for example, has 500 dot memories *1, *2, ..., *500, which numbers correspond to the horizontal addresses and indicate that the thermal imaging apparatus has 500 picture elements in the horizontal direction of the FOV.

As described above, in the thermal imaging apparatus of the prior art, the video signals of one frame of the optical scanning by the IR CAM 1 are memorized in the MEM 3 using all of its dot memories, the video data of the MEM 3 are read out and displayed on the TV MON 7, using all of the area of the monitor screen. This means that the thermal images corresponding to different times could not be displayed on the TV monitor at the same time.

One method to solve this problem is to increase the capacity with a hard memory, by applying the usual technique with a hard memory, so that all of the data of the thermal images at different times can be memorized and simultaneously displayed on respective parts of the monitor.

Figure 4:
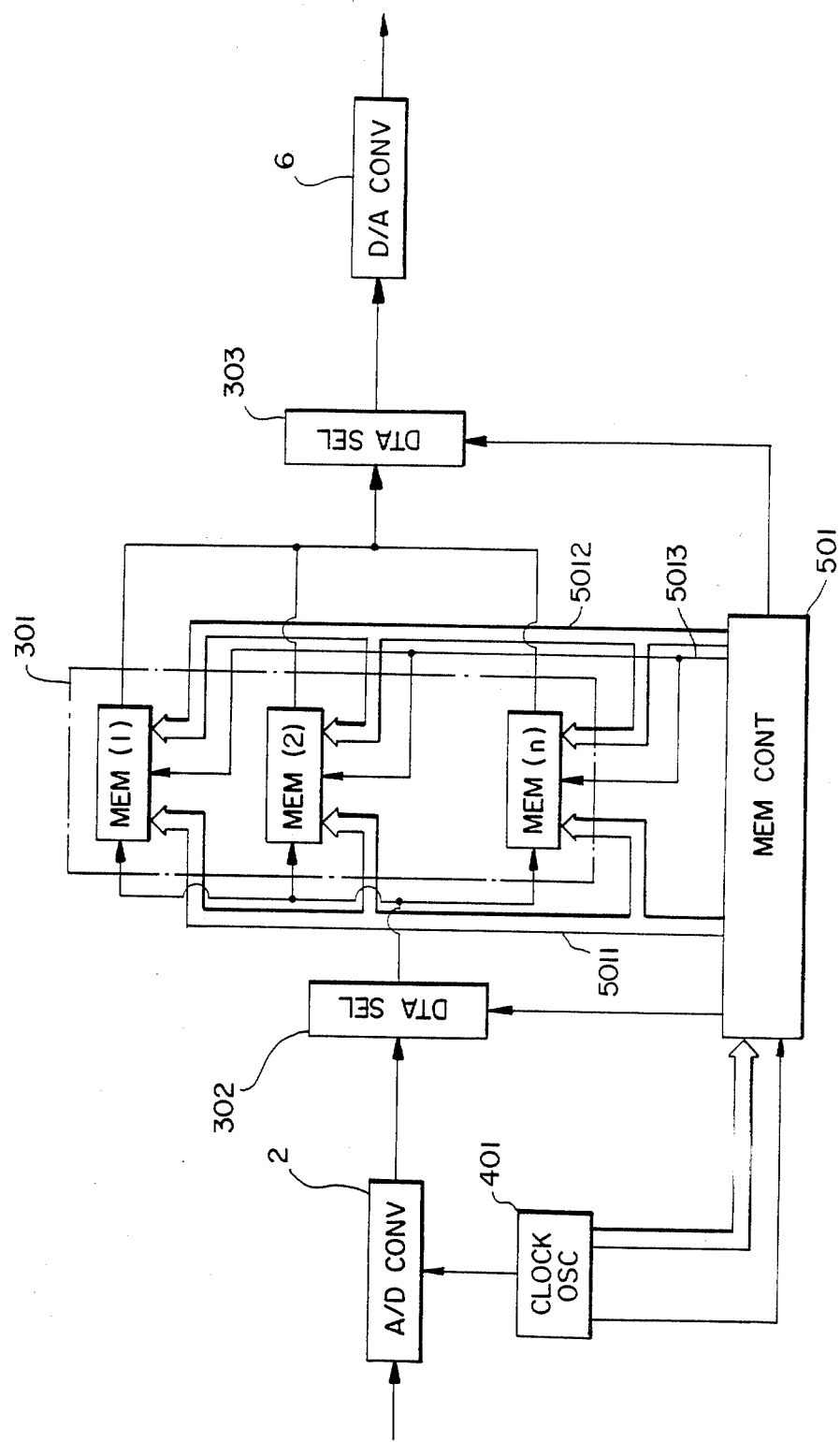
FIG. 4 is a block diagram of a conventional hard memory having a large capacity of the memory dots and conventional adjacent control units, as in the thermal imaging apparatus of the prior art of FIG. 2, so that the hard memory can memorize the image data of a number of the optical scanning frames.

FIG. 4 is a block diagram showing a hard memory having a large capacity of the memory dots and the usual adjacent control units of a thermal imaging apparatus of the prior art as in Fig. 2, so that the hard memory can memorize the image data of a number of the optical scanning frames, the figure showing memory space for n frames. In the figure, reference numeral 301 is a large hard memory MEM, 401 is a clock oscillator CLOCK OSC, 501 is a memory controller MEM CONT, 302 is an input data selector DTA SEL, 303 is an output data selector DTA SEL, and the A/D CONV 2 and the D/A CONV 6 have the same function as in FIG. 2.

As shown in the figure, the MEM 301 has enough memory dots to memorize all the image data at different times. Each block memory MEM(1), MEM(2), ..., and MEM(n) is for the memory dots corresponding to a respective frame of optical scanning. Here, "n" means that n frames can be memorized, that is, n thermal images are intended to be displayed on the TV monitor at once.

A main unit to control the MEM 301 is the MEM CONT 501 which controls the DTA SEL 302, the large hard memory 301, and DTA SEL 303, upon receiving a timing signal (through the solid-line connection), and a write-in address control signal (through the illustrated double-line connection, conventionally indicating parallel bit data transfer) from the CLOCK OSC 401. The MEM CONT 501 controls the block memories to switch the operation of the write-in or read-out of the image data for the block memories, through the solid-line connection 5013.

The digital video signals from the A/D CONV 2 are selected by the DTA SEL 302 in accordance with a control signal from the MEM CONT 501, so that the group of the digital video signals of each frame of optical scanning are memorized in a designated block memory. The memorization can be made also by the control of the write-in address signals from the MEM CONT 501 through the double-line 5011.

The image data memorized in the MEM 301 are read out by the read-out address signals from the MEM CONT 501 through the double-line connection 5012, and are sent to the DTA SEL 303 which controls the timing for the read-out video signal. The output from the DTA SEL 303 goes to the D/A CONV 6 and the digital video signals are displayed on the TV monitor, so that n thermal time images of an observed object are simultaneously displayed on a TV monitor screen.

If the thermal imaging apparatus uses the large hard memory 301 as mentioned above, it will be possible to realize simultaneous observation of the thermal time images on a TV monitor screen. However, it is also an obvious fact that a high cost is associated with the large hard memory and the complicated control that is required. Therefore, it can be said that while a thermal imaging apparatus using a large hard memory can be considered in principle, it is impossible to actually realize it from an economical viewpoint, as mentioned before.

The thermal imaging apparatus of the present invention solves the problem of cost. The present invention will be discussed in connection with the preferred embodiments of FIGS. 5 and 6. Each embodiment uses a hard memory having the same capacity of the MEM 3 in FIG. 2, however the way the hard memory is used is quite different from that of the prior art.

Figure 5:
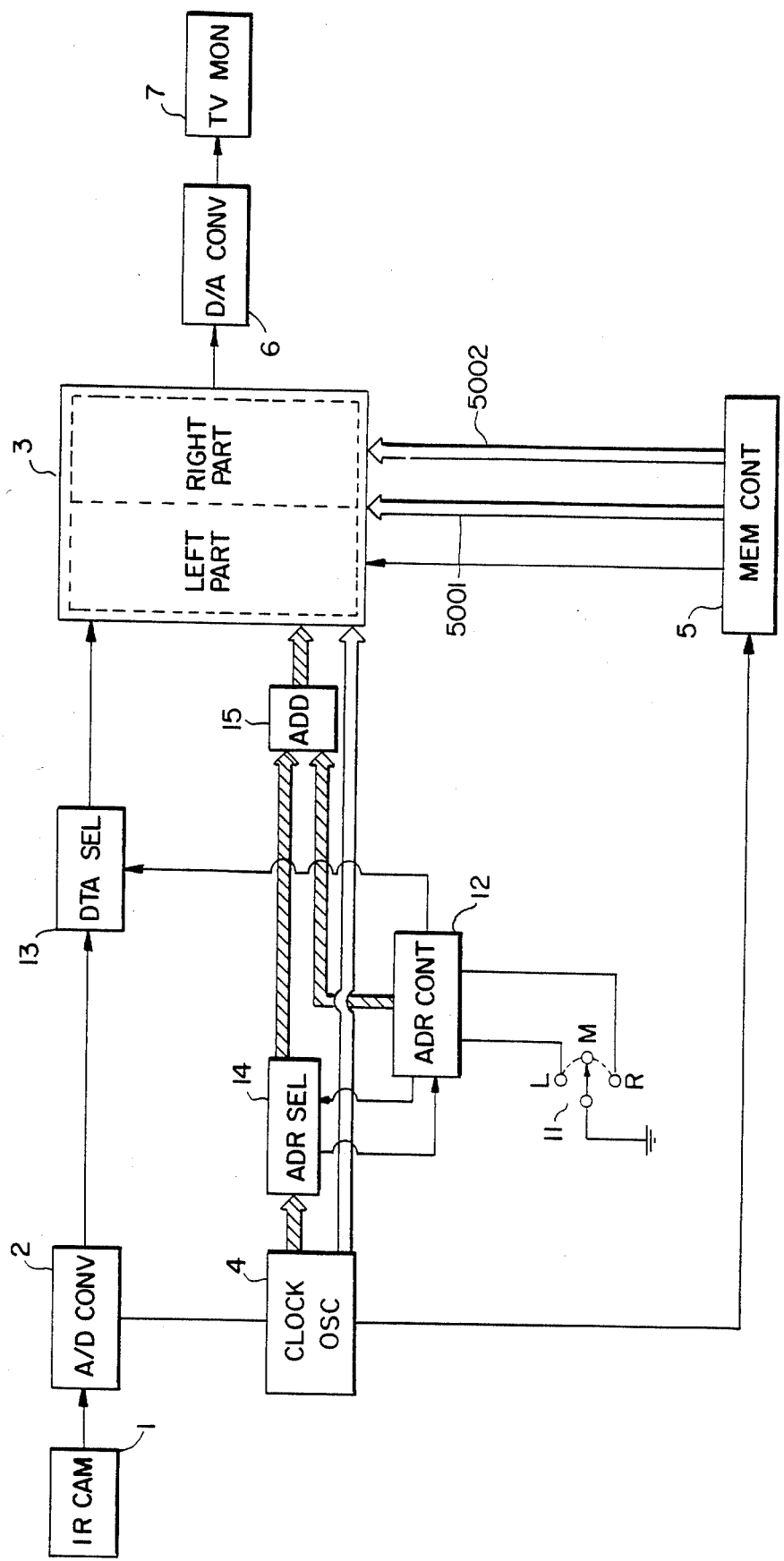
FIG. 5 is a block diagram of an embodiment of the present invention which can simultaneously display two thermal time images on left and right portions of the TV monitor screen.

In the embodiments of FIGS. 5 and 6, the hard memory memorizes image data of two frames of respective optical scannings, and two thermal time images can be simultaneously displayed in left and right parts of the TV screen as in FIG. 5, or in upper and lower parts of the TV screen as in FIG. 6.

FIG. 5 is a block diagram of an embodiment of the present invention which uses a hard memory to memorize image data corresponding to two thermal images at different times, in the left and right parts. In the figure, the blocks having the same reference numerals as in FIG. 2 have the same function as in Fig. 2. Reference numeral 11 is a left-middle-right switch SWT, 12 is an address controller ADR CONT, 13 is a data selector DAT SEL, 14 is an address selector ADR SEL, and 15 is an adder ADD. Further, in the figure, the double-line connection between the CLOCK OSC 4 and the MEM 3 are is for the vertical write-in address signals for the MEM3, whereas the double-line connections filled with the oblique lines are for the horizontal write-in address signals.

In FIG. 5, the SWT 11 is switched by the operator. When the SWT 11 is switched to the middle position M, the thermal imaging apparatus (referred to as "the apparatus" hereinafter) works in a single-mode, that is, in the same way as that of FIG. 2. When it is switched to the left L or right R position, the apparatus works in a multi-mode. That is, when the switch 11 is at L, the IR CAM 1 is directed by the operator so that the observed object is in the left half of the FOV, at time $t_1$, and then the operator switches the SWT 11 from L to R at the time $t_2$, so that the image data of the observed object of the two times are memorized in the left and right halves L and R of the memory MEM 3, corresponding to respective groupings of the memory dots in the display. Consequently, the read-out thermal images at the time $t_1$ and $t_2$ can be simultaneously displayed on a single screen of the TV MON 7. The actual process for performing the above function is as follows.

In FIG. 5, the vertical write-in address signals go directly to the MEM 3 from the CLOCK OSC 4 and control the vertical addresses of the MEM 3. However, the horizontal write-in address signals are controlled by the additional units including the SWT 11, the ADR CONT 12, the ADR SEL 14, and the ADD 15. Further, the DTA SEL 13 is added between the A/D CONV 2 and the MEM 3 to control the digital video signals to be memorized in the MEM 3.

When the SWT 11 is switched to the middle position M, the ADR CONT 12 sends a signal of the value "0" to the ADD 15 and controls the ADR SEL 14 to be ON, so that the write-in address signals from the CLOCK OSC 4 go to the MEM 3. The ADR CONT 12 controls the DTA SEL 13 to be ON, so that the digital video signals from the A/D CONV 2 go to the MEM 3. As a result, the digital video signals for one frame of optical scanning are memorized in all of the memory dots, one after another in the same way as explained in FIG. 2.

The function of the MEM CONT 5 is the same as of the MEM CONT 5 or the prior art of FIG. 2, but in FIG. 5, the read-out signals are shown in more detail by the two pairs of double-line connections, 5001 for horizontal and 5002 for vertical read-out address signals. By the control of the MEM CONT 5, a thermal time image is displayed on the screen of the TV MON 7 in the single-mode operation.

When the apparatus is required to change its mode from single-mode to multi-mode, the IR CAM 1 is directed so that an observed object in the left half of the FOV, according to the above example, and the SWT 11 is switched into the L position. The ADR CONT 12 sends a signal for example of logic value 0 to the ADD 15 and controls the ADR SEL 14, so that the horizontal write-in address signals from the CLOCK OSC 4 are allowed to pass to the MEM 3. The ADR SEL 14 sends a signal of the value "250" back to the ADR CONT 12, and the ADR CONT 12 controls the DTA SEL 13, so that the digital video signals for the limits of the addresses from *1 to *250 (see FIG. 3) go to the MEM 3 from the A/D CONV 2, and the other digital video signals for the addresses from *251 to *500 are rejected and the "0" signals are sent to the MEM 3. As a result, in the MEM 3, the image data of the horizontal addresses from *1 to *250 are memorized and the other memory dots of the horizontal addresses from *251 to *500 are cleared.

Next, when the SWT 11 is switched into the R position, while keeping the direction of the IR CAM 1 in the state mentioned above, the ADR CONT 12 sends a signal of the value "250" to the ADD 15, controls the DTA SEL 13 to be ON and controls the ADR SEL 14 so that only the write-in address signals from *1 to *250 go to the MEM 3. By doing so, the image data of the same observed object at the later time can be memorized in the horizontal addresses from *251 to *500, while the image data which have been memorized in the horizontal addresses from *1 to *250 is retained.

Consequently, the image data at the earlier time $t_1$ can be memorized in the left half and the image data at the later time $t_2$ can be memorized in the right half of the memory dots of the MEM 3. Therefore, two thermal time images at different times $t_1$, $t_2$ can be simultaneously compared with each other on the screen of the TV MON 7.

FIG. 6 shows a block diagram of another embodiment of the present invention. In FIG. 6, the units having the same numerals as in FIG. 5 have the same function. However, in this case, the switching positions of the SWT 11 are upper U and lower L positions, instead of L and R as in FIG. 5. Reference numeral 17 is an address controller ADR CONT, 18 is an address selector ADR SEL, and 19 is an adder ADD. The double lines between the CLOCK OSC 4 and the MEM 3 are for the write-in address signals, wherein the double lines marked by the oblique lines are for the vertical write-in address signals.

The apparatus of this embodiment also has two operational modes, namely, a single-mode and a multi-mode as in the former embodiment.

In FIG. 6, the horizontal write-in address signals go directly to the MEM 3 from the CLOCK OSC 4 and control the horizontal addresses of the MEM 3 in the same way as in FIG. 2. However, the vertical write-in address signals are controlled by the additional units including the SWT 11, the ADR CONT 17, the ADR SEL 18, and the ADD 19. When the multi-mode operation is required, the SWT 11 is switched into U and L positions, and the IR CAM 1 is directed so that an observed object is in the upper half of the FOV. When the SWT 11 is switched from U to L at the time $t_2$, respectively, the ADR CONT 17 controls the DTA SEL 13, the ADR SEL 18, and indirectly the ADD 19 through the ADR SEL 18, so that the image data of the observed object at different times $t_1$ and $t_2$ are memorized sequentially in the upper and the lower halves of the memory dots in the MEM 3. This operation is similar to that in FIG. 5, that is, the image data at the first time $t_1$ are memorized in the upper half of the memory dots, while the memory dots of the lower half of the memory MEM 3 are cleared as the first step, and, in the second step, the image data at the time $t_2$ are memorized in a lower half of the memory dots, while holding the image data of the first step in the upper half of the memory dots. The image data memorized in the MEM 3 are then read out by the control of the MEM CONT 5 as in the case of FIG. 5, so that two thermal time images can be simultaneously compared with each other in the upper and lower halves of the TV monitor screen.

Furthermore, though a block diagram is not shown, the embodiments of FIGS. 5 and 6 may be combined, to simultaneously display four thermal time images on a screen of the TV monitor. FIG. 7 shows the illustration of the screen where four thermal time images are displayed.

As a final result, it can be said that, by the thermal imaging apparatus of the present invention, a plurality of thermal images of an observed object corresponding to different times can be simultaneously observed and compared on a single screen of the TV monitor with a simple and economical apparatus.

Furthermore, the present invention can be applied to not only the thermal imaging apparatus but also to other imaging apparatuses having a scanning sensor and a displaying device, wherein a plurality of the sensed images of an object to be observed or inspected at different times can be simultaneously provided on a single screen of the displaying device, to obtain information by comparing the sensed images with each other.

What is claimed is:

1. An imaging apparatus comprising
sensing means for providing image data of an observed object by scanning an instantaneous sensing field at a first speed across a total sensing field which includes said observed object,
a display means including a screen for displaying, at a second speed that is different from said first speed, a sensed image of said observed object according to said image data,
a digital semiconductor memory device for writing into respective memory elements at said first speed said image data from said sensing means, and for reading out data stored in said memory device at said second speed to said display means,
means for selectively determining said total sensing field of said sensing means so that said observed object is in a predetermined limited part of said total sensing field,
means for writing a limited part of said image data, corresponding to said limited part of said total sensing field, into a respective limited region of said memory device, and
means for subsequently writing at least one further one of said limited part of said image data, each corresponding to a respective sensed image of said object in said limited part of said total sensing field at a respective different time, at said first speed, into respective regions of said memory device, while maintaining the previously written at least one limited part of said image data, each said limited part of said image data corresponding to a respective thermal image to be simultaneously displayed, in respective limited parts of said memory device,
wherein a plurality of said sensed images corresponding to said plurality of said limited image data are read out from said memory device at said second speed for simultaneous display on said screen.

2. The imaging apparatus according to claim 1, wherein
said sensing means includes an infrared camera which scans said observed object in said total sensing field including said limited part thereof with said instantaneous sensing field at said first speed, and
said displaying means including a television monitor with a screen for displaying a thermal image of said observed object at said second speed, said second speed being a television displaying speed which is higher than said first speed of said scanning.

3. The apparatus of claim 1, wherein each said limited part of said image data, corresponding to each respective time and region of said memory device, is provided by said sensing means during a respective scanning of said total sensing field.

4. The apparatus of claim 3, wherein the capacity of said memory device is limited to that required for displaying all of said image data corresponding to said total sensing field and to a single time.

5. An image sensing apparatus comprising
a sensing means for providing image data of an object under observation by scanning at a first speed a total sensing field which includes said object,
a digital semiconductor memory device for storing at said first speed said image data, including for selectively storing at respective different regions thereof a limited part of said image data corresponding to a respective limited part of said total sensing field for a plurality of respective different times, and for reading out the stored data at a second speed,
wherein the apparatus is selectively operable to simultaneously display said limited parts of said image data of said respective different times, corresponding to said limited part of said total sensing field at said different times, in respective different parts of said display.

6. The apparatus of claim 5, wherein the capacity of said memory device is only large enough to store one set of said image data corresponding to said total sensing field.

7. The apparatus of claim 5, comprising means for selectively switching between displaying the data of the entirety of said total sensing field, for at least one respective time of observing said object, and displaying said limited part of said data corresponding to said limited part of said total sensing field including said object for a respective plurality of times of observing said object.

8. The apparatus of claim 5, said second speed being different from said first speed.

9. The apparatus of claim 5, wherein each said limited part of the image data, corresponding to a respective different time, all correspond to the same limited part of said total sensing field, said sensing means being controlled so that said observed object is held in said same limited part of said total sensing field for all of said different times.

10. The apparatus of claim 9, wherein the capacity of said memory device is only large enough to store one set of said image data corresponding to the entirety of said total sensing field.

* * * * *